US008389580B2

(12) United States Patent
McCafferty et al.

(10) Patent No.: US 8,389,580 B2
(45) Date of Patent: Mar. 5, 2013

(54) ARYLCYCLOPROPYLAMINES AND METHODS OF USE

(75) Inventors: Dewey G. McCafferty, Durham, NC (US); Julie Pollock, Durham, NC (US)

(73) Assignee: Duke University, Durham, NC (US)

( * ) Notice: Subject to any disclaimer, the term of this patent is extended or adjusted under 35 U.S.C. 154(b) by 272 days.

(21) Appl. No.: 12/792,316

(22) Filed: Jun. 2, 2010

(65) Prior Publication Data
US 2010/0324147 A1 Dec. 23, 2010

Related U.S. Application Data

(60) Provisional application No. 61/184,505, filed on Jun. 5, 2009, provisional application No. 61/183,421, filed on Jun. 2, 2009.

(51) Int. Cl.
*A61K 31/135* (2006.01)
*C07C 211/00* (2006.01)
(52) U.S. Cl. ........................................ 514/647; 564/307
(58) Field of Classification Search .................. 514/647; 564/307
See application file for complete search history.

(56) References Cited

U.S. PATENT DOCUMENTS
2010/0324147 A1 12/2010 McCafferty et al.

FOREIGN PATENT DOCUMENTS

| WO | WO 97/22596 | 6/1997 |
|---|---|---|
| WO | WO 97/30035 | 8/1997 |
| WO | WO 97/32856 | 9/1997 |
| WO | WO 98/13354 | 4/1998 |
| WO | WO 98/35985 | 8/1998 |
| WO | WO 99/02166 | 1/1999 |
| WO | 99/05143 | 2/1999 |
| WO | WO 00/40529 | 7/2000 |
| WO | WO 00/41669 | 7/2000 |
| WO | WO 00/47212 | 8/2000 |
| WO | WO 01/60814 | 8/2001 |
| WO | WO 01/92224 | 12/2001 |
| WO | WO 01/94341 | 12/2001 |
| WO | WO 02/04434 | 1/2002 |
| WO | WO 02/08213 | 1/2002 |

OTHER PUBLICATIONS

Pannala et al. CAS: 148:11050, 2007.*
Guile et al. CAS: 130: 168386, 1999.*
Burger et al. CAS: 48: 18115, 1954.*
2009 poster presentation.
Arvidsson, L. et al., "N,N-Dialkylated Monophenolic trans-2-Phenylcyclopropylamines: Novel Central 5-Hydroxytryptamine Receptor Agonists" J. Med. Chem. (1988) 31:92-99.
Berge et al., "Pharmaceutical Salts" J. Pharm. Sci. (1977) 66:1-19.
Binda, C. et al., "Insights into the mode of inhibition of human mitochondrial monoamine oxidase B from high-resolution crystal structures" Proc. Natl. Acad. Sci. USA (2003) 100:9750.
Burger, A. et al., "Arylcycloalkylamines. I. 2-Phenylcyclopropylamine" J. Am. Chem. Soc. (1948) 70:2198.
Ciaccio, J.A. et al., ""Instant Methylide" Modification of the Corey-Chaykovsky Cyclopropanation Reaction" Synth. Commun. (2006) 36:1333.
Cloos, P.A.C. et al., "The putative oncogene GASC1 demethylates tri- and dimethylated lysine 9 on histone H3" Nature (2006) 442:307.
Corey, E.J. et al., "Dimethyloxosulfonium Methylide ((CH3)2SOCH2) and Dimethylsulfonium Methylide ((CH3)2SCH2). Formation and Application to Organic Synthesis" J. Am. Chem. Soc. (1965) 87:1353.
Corey, E.J. et al., "Dimethylsulfoxonium Methylide" J. Am. Chem. Soc. (1962) 86:867.
Forneris, F. et al., "Histone demethylation catalysed by LSD1 is a flavin-dependent oxidative process" FEBS Lett. (2005) 579:2203.
Gooden, D.M. et al., "Facile synthesis of substituted trans-2-arylcyclopropylamine inhibitors of the human histone demethylase LSD1 and monoamine oxidases A and B," Biorg. Med. Chem. Left. (2008) 18:3047-3051.
Hakimi, M-A. et al., "A Candidate X-linked Mental Retardation Gene Is a Component of a New Family of Histone Deacetylase-containing Complexes" J. Biol. Chem. (2003) 278:7234-7239.
He et al., "Regulation of Flowering Time by Histone Acetylation in Arabidopsis" Science (2003) 302:1751-1754.
He, S. et al., "Facile synthesis of site-specifically acetylated and methylated histone proteins: Reagents for evaluation of the histone code hyposthesis" Proc. Natl. Acad. Sci. (7003) 100:17033-17038.
Klose, R.J. et al., "The transcriptional repressor JHDM3A demethylates trimethyl histone H3 lysine 9 and lysine 36" Nature (2006) 442:312.
Lee et al., "Histone H3 Lysine 4 Demethylation Is a Target of Non-selective Antidepressant Medications" Chem. Biol. (2006) 13:563-.
McCafferty, D.G., "Synthesis and evaluation of trans-2-arylcyclopropylamine-based inhibiltors of lysine-specific demethylase 1" Division of Medicinal Chemistry Abstracts—235th ACS National Meeting, Apr. 6-10, 2008, http://www.acsmedchem.org/mediabstracts2008.pdf.
Rosen, T. et al., "Fluorinated Phenylcyclopropylamines. 2. Effects of Aromatic Ring Substitution and of Absolute Configuration on Inhibition of Microbial Tyramine Oxidase" J. Med. Chem. (2004) 47:5860.
Schmidt, D.M.Z. et al., "trans-2-Phenylcyclopropylamine Is a Mechanism-Based Inactivator of the Histone Demethylase LSD1" Biochem. (2007) 46:4408-4416.
Shi, Y. et al., "Histone Demethylation Mediated by the Nuclear Amine Oxidase Homolog LSD1" Cell (2004) 119:941.
Stern et al., "Overview of monoclonal antibodies in cancer therapy: present and promise" Critical reviews in oncology/haematology, (2005) 54:11-29.
Szewczuk, L. et al., "Mechanistic Analysis of a Suicide Inactivator of Histone Demethylase LSD1" Biochem. (2006) 46:6892.
Tichilibon, S. et al., "Exploring distal regions of the A3 adenosine receptor binding site: sterically constrained N6-(7-phenylethyl)adenocine derivatives as potent ligands" Bioorg. Med. Chem. (7004)17:7071.
Tsukada, Y. et al., "Histone demethylation by a family of JmjC domain-containing proteins" Nature (2006) 439:811.
Vallgarda, J. et al., "trans-2-Aryl-N,N-dipropylcyclopropylamines: Synthesis and Interactions with 5-HT1A Receptors" J. Med. Chem. (1996) 39:1485.
Whetstine, J.R. et al., "Reversal of Histone Lysine Trimethylation by the JMJD2 Family of Histone Demethylases" Cell (2006) 125:467.

(Continued)

*Primary Examiner* — Rei-tsang Shiao
(74) *Attorney, Agent, or Firm* — Michael Best & Friedrich LLP

(57) ABSTRACT

Described herein are arylcyclopropylamine compounds that may inhibit enzymes comprising an amine oxidase domain, such as LSD1, MAO A and/or MAO B.

8 Claims, 4 Drawing Sheets

OTHER PUBLICATIONS

Yamane, K. et al., "JHDM2A, a JmjC-Containing H3K9 Demethylase, Facilitates Transcription Activation by Androgen Receptor" Cell (2006) 125:483.

Yang, M. et al., "Structural Basis for the Inhibition of the LSD1 Histone Demethylase by the Antidepressant trans-2-Phenylcyclopropylamine" Biochemistry (2007) 46:8058.

Zhang, Y. et al., "Transcription regulation by histone methylation: interplay between different covalent modifications of the core histone tails" Genes Dev. (2001) 15:2343.

Burger et al., "Arylcycloalkylamines. III. 2-(3,4-Dimethoxyphenyl)-cyclopropylamine," Journal of the American Chemical Society, 1952, Vol. 74, Issue 13, pp. 3415-3416.

Pannala et al., "Synthesis and structure—activity relationship of 4-(2-aryl-cyclopropylamino)-quinoline-3-carbonitriles as EGFR tyrosine kinase inhibitors," Bioorganic & Medicinal Chemistry Letters, 2007, vol. 17, pp. 5978-5982.

* cited by examiner

Table 1. Kinetic parameters for inactivation of LSD1, MAO B and MAO A by arylcyclopropylamine compounds
| entry | Inhibitor | LSD1 | | |
|---|---|---|---|---|
| | | $k_{inact}$ (s$^{-1}$) | $K_I$ (μM) | $k_{inact}/K_I$ (M$^{-1}$ s$^{-1}$) |
| 1 | 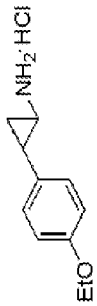 | 0.0204 ± 0.0018 | 456 ± 86 | 45 |
| 2 | 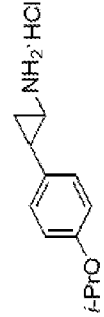 | 0.0192 ± 0.0017 | 352 ± 76 | 54 |
| 3 | 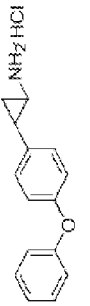 | 0.0175 ± 0.0017 | 296 ± 77 | 59 |
| 4 | 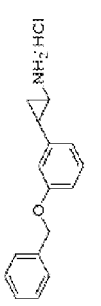 | 0.0253 ± 0.0052 | 760 ± 280 | 33 |
| 5 | 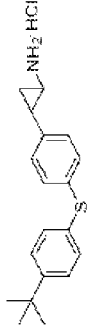 | 0.0215 ± 0.0030 | 540 ± 160 | 40 |
FIGURE 2 (1 of 3)

Table 1. Kinetic parameters for inactivation of LSD1, MAO B and MAO A by arylcyclopropylamine compounds

| entry | Inhibitor | MAO B | | |
|---|---|---|---|---|
| | | $k_{inact}$ (s$^{-1}$) | $K_i$ (μM) | $k_{inact}/K_i$ (M$^{-1}$ s$^{-1}$) |
| 1 | EtO-C₆H₄-cyclopropyl-NH₂·HCl | 0.048 ± 0.004 | 63 ± 10 | 762 |
| 2 | i-PrO-C₆H₄-cyclopropyl-NH₂·HCl | 0.046 ± 0.006 | 106 ± 20 | 383 |
| 3 | PhO-C₆H₄-cyclopropyl-NH₂·HCl | 0.0323 ± 0.0018 | 29.5 ± 4.4 | 1095 |
| 4 | BnO-C₆H₄-cyclopropyl-NH₂·HCl | not tested | | |
| 5 | t-Bu-C₆H₄-S-C₆H₄-cyclopropyl-NH₂·HCl | not tested | | |

FIGURE 2 (2 of 3)

Table 1. Kinetic parameters for inactivation of LSD1, MAO B and MAO A by arylcyclopropylamine compounds
| entry | Inhibitor | MAO A | | |
|---|---|---|---|---|
| | | $k_{inact}$ (s$^{-1}$) | $K_I$ (μM) | $k_{inact}/K_I$ (M$^{-1}$ s$^{-1}$) |
| 1 | 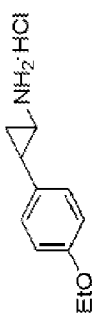 | 0.0135 ± 0.0004 | 4.3 ± 0.8 | 3140 |
| 2 | 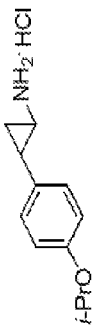 | 0.026 ± 0.002 | 19.7 ± 4.6 | 1319 |
| 3 | 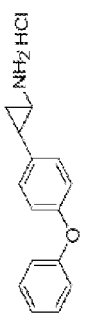 | 0.071 ± 0.007 | 12.4 ± 4.3 | 5725 |
| 4 | 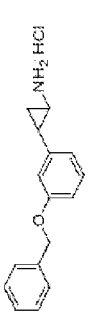 | not tested | | |
| 5 | 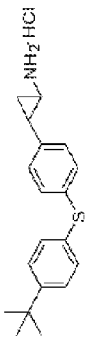 | not tested | | |
FIGURE 2 (3 of 3)

ARYLCYCLOPROPYLAMINES AND METHODS OF USE

CROSS-REFERENCE TO RELATED APPLICATIONS

This application claims priority under 35 U.S.C. §119(e) to U.S. Provisional Patent Application No. 61/183,421, filed Jun. 2, 2009, and U.S. Provisional Patent Application No. 61/184,505, filed Jun. 5, 2009, each of which is incorporated by reference in its entirety.

STATEMENT REGARDING FEDERALLY SPONSORED RESEARCH

This invention was made with US Government support awarded by National Institutes of Health, Grant No. GM65539. The United States has certain rights in this invention.

BACKGROUND OF THE INVENTION

The functional capacity of genetically encoded proteins is powerfully expanded by reversible posttranslational modification. Within eukaryotic cells, the regulation of gene expression is intimately linked with posttranslational modification of histone proteins. Reversible histone posttranslational modifications include acetylation of lysine, phosphorylation of serine and threonine, and methylation of lysine and arginine. The resulting complexity of modifications has been postulated to act as a 'histone code,' by which these patterns of modifications are 'read' by cellular machinery to produce a specific gene regulatory outcome.

One class of human enzymes capable of demethylating lysine residues includes the amine oxidase domain-containing lysine specific demethylase 1 (LSD1). Catalysis by LSD1 is a flavin-dependent process in which formaldehyde and peroxide are produced as by-products of histone demethylation. The amine oxidase domain of LSD1 is homologous to equivalent domains found in monoamine oxidases A and B (MAO A, 17.6% identity; MAO B, 17.6% identity). Inhibitors of LSD1 and/or of monoamine oxidases A and B may have therapeutic utility.

SUMMARY OF THE INVENTION

In one aspect, the invention may feature a compound according to formula (I):

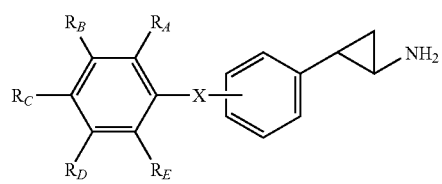

(I)

wherein:
X is selected from a bond, O, S, and NH; and
$R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and isomers, prodrugs and salts thereof.

In another aspect, the invention may feature a compound according to formula (VIII):

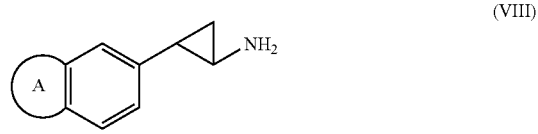

(VIII)

wherein:
A is a $C_5$-$C_6$ aryl, cycloalkenyl or heterocyclyl ring.

In another aspect, the invention may feature a compound according to formula (XIII):

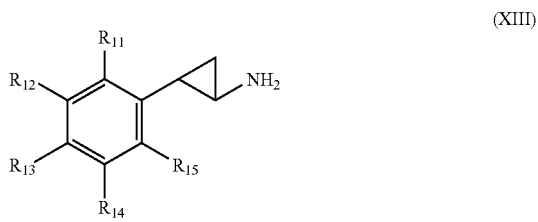

(XIII)

wherein $R_{11}$, $R_{12}$, $R_{13}$, $R_{14}$ and $R_{15}$ are independently selected from hydrogen, $C_{1-7}$ alkyl, $C_{3-20}$ heterocyclyl, $C_{2-7}$ alkoxy, amino, cyano, nitro, ether and thioether; and isomers, prodrugs and salts thereof.

In another aspect, the invention may feature a pharmaceutical composition comprising a compound described herein and a pharmaceutically acceptable carrier.

In another aspect, the invention may feature a method of inhibiting an enzyme comprising an amine oxidase domain, the method comprising contacting a cell with an effective amount of a compound described herein.

In another aspect, the invention may feature a method of treating cancer in a subject, comprising administering to the subject an effective amount of a compound described herein.

In another aspect, the invention may feature a method of treating a central nervous system disorder in a subject, comprising administering to the subject an effective amount of a compound described herein.

BRIEF DESCRIPTION OF THE DRAWINGS

FIG. 2 shows kinetic parameters for inactivation of LSD1, MAO B and MAO A by arylcyclopropylamine compounds.

DETAILED DESCRIPTION OF THE INVENTION

Figure 1:
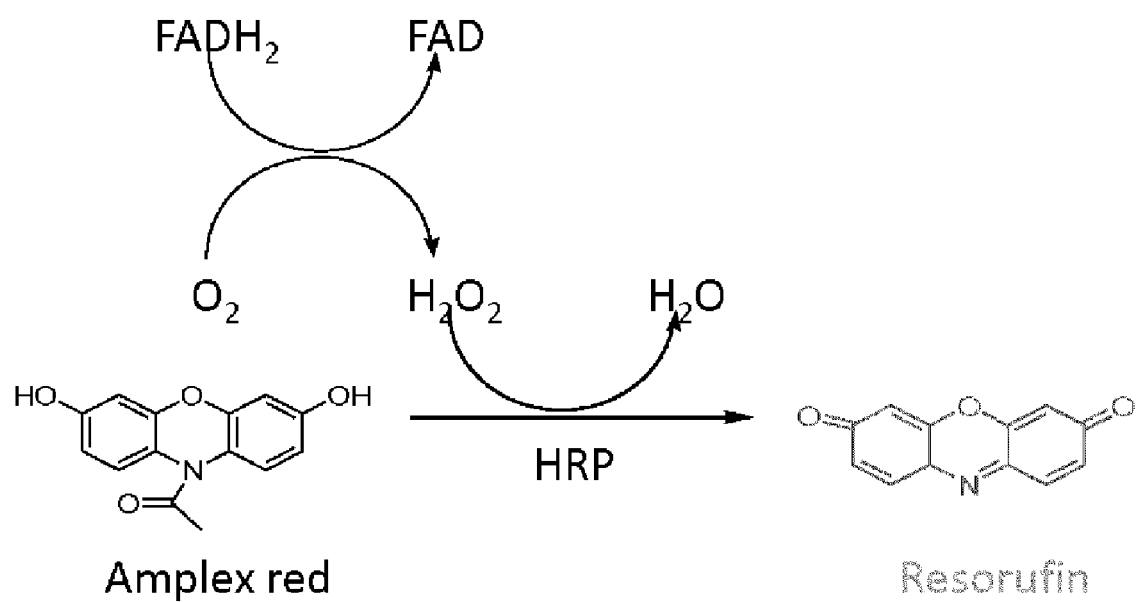
FIG. 1 shows a horseradish peroxidase (HRP) coupled assay used to monitor amine oxidase activity of LSD1 or MAOs, used to assay the compounds of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The invention generally relates to arylcyclopropylamine compounds that may inhibit enzymes comprising an amine oxidase domain, such as LSD1, MAO A and/or MAO B.

DEFINITIONS $C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Suitably, each ring has from 5 to 7 ring atoms.

The ring atoms may be all carbon atoms, as in "carboaryl groups", in which case the group may conveniently be referred to as a "$C_{5-20}$ carboaryl" group. Examples of $C_{5-20}$ aryl groups which do not have ring heteroatoms (i.e. $C_{5-20}$ carboaryl groups) include, but are not limited to, those derived from benzene (i.e. phenyl) (C6), naphthalene (C10), anthracene (C14), phenanthrene (C14), naphthacene (C18), and pyrene (C16).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Suitably, each ring has from 5 to 7 ring atoms, of which from 0 to 4 are ring heteroatoms. Examples of $C_{5-20}$ heteroaryl groups include, but are not limited to, C5 heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole, oxadiazole (furazan) and oxatriazole; and C6 heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The above $C_{5-20}$ aryl groups whether alone or part of another substituent, may themselves optionally be substituted with one or more groups selected from themselves and the additional substituents listed below.

$C_{1-7}$ alkyl: The term "$C_{1-7}$ alkyl", as used herein, pertains to a monovalent moiety obtained by removing a hydrogen atom from a hydrocarbon compound having from 1 to 7 carbon atoms, which may be aliphatic or alicyclic, or a combination thereof, and which may be saturated, partially unsaturated, or fully unsaturated. Suitably, the alkyl group contains from 3 to 7 carbon atoms, i.e. is a "$C_{3-7}$ alkyl".

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, di methylcyclobutyl, methylcyclopentyl, di methylcyclopentyl, methylcyclohexyl, di methylcyclohexyl, cyclopropylmethyl and cyclohexylmethyl.

Examples of unsaturated $C_{1-7}$ alkyl groups which have one or more carbon-carbon double bonds (also referred to as "$C_{2-7}$ alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 atoms, of which from 1 to 10 are ring heteroatoms, and wherein at least one of said ring(s) is a heterocyclic ring. Suitably, each ring has from 3 to 7 ring atoms, of which from 1 to 4 are ring heteroatoms. Ring heteroatoms may be selected from the group consisting of O, N, S and P. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran (C6), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulfur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulfur ring atom include, but are not limited to, those derived from oxathiolane and oxathiane (thioxane).

Examples of $C_{3-20}$ heterocyclyl groups having one nitrogen ring atom and one sulfur ring atom include, but are not limited to, those derived from thiazoline, thiazolidine, and thiomorpholine.

Other examples of $C_{5-20}$ heterocyclic groups (some of which are $C_{5-20}$ heteroaryl groups) which comprise fused rings, include, but are not limited to, C9 heterocyclic groups derived from benzofuran, isobenzofuran, indole, isoindole, purine (e.g., adenine, guanine), benzothiophene, benzimidazole; C10 heterocyclic groups derived from quinoline, isoquinoline, benzodiazine, pyridopyridine, quinoxaline; C13 heterocyclic groups derived from carbazole, dibenzothiophene, dibenzofuran; C14 heterocyclic groups derived from acridine, xanthene, phenoxathiin, phenazine, phenoxazine, phenothiazine.

Other examples of $C_{3-20}$ heterocyclyl groups include, but are not limited to, oxadiazine and oxathiazine.

Examples of heterocyclyl groups which additionally bear one or more oxo (=O) groups, include, but are not limited to, those derived from: C5 heterocyclics, such as furanone, pyrone, pyrrolidone (pyrrolidinone), pyrazolone (pyrazolinone), imidazolidone, thiazolone, and isothiazolone; C6 heterocyclics, such as piperidinone (piperidone), piperidinedione, piperazinone, piperazinedione, pyridazinone, and pyrimidinone (e.g., cytosine, thymine, uracil), and barbituric acid; fused heterocyclics, such as oxindole, purinone (e.g., guanine), benzoxazolinone, benzopyrone (e.g., coumarin); cyclic anhydrides (—C(=O)—O—C(=O)— in a ring), including but not limited to maleic anhydride, succinic anhydride, and glutaric anhydride; cyclic carbonates (—O—C(=O)—O— in a ring), such as ethylene carbonate and 1,2-propylene carbonate; imides (—C(=O)—NR—C(=O)— in a ring), including but not limited to, succinimide, maleimide, phthalimide, and glutarimide; lactones (cyclic esters, —O—C(=O)— in a ring), including, but not limited to, β-propiolactone, γ-butyrolactone, δ-valerolactone (2-piperidone), and ε-caprolactone; lactams (cyclic amides, —NR—C(=O)— in a ring), including, but not limited to, β-propiolactam, γ-butyrolactam (2-pyrrolidone), δ-valerolactam, and ε-caprolactam; cyclic carbamates (—O—C(=O)—NR— in a ring), such as 2-oxazolidone; cyclic ureas (—NR—C(=O)—NR— in a ring), such as 2-imidazolidone and pyrimidine-2,4-dione (e.g., thymine, uracil).

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), a $C_{5-20}$ aryl group (also referred to as a $C_{5-20}$ aryloxy group), or a $C_{5-20}$ arylalkyl group (also referred to as a $C_{5-20}$ arylalkyloxy group), for example, a benzyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl). Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR1R2, wherein R1 and R2 are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R1 and R2, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR1C(=O)R2, wherein R1 is an amide substituent, for example, hydrogen, a $C_{1-7}$ alkyl group, a $C_{3-20}$ heterocyclyl group, or a $C_{5-20}$ aryl group, and R2 is an acyl substituent, for example, a $C_{1-7}$ alkyl group, a $C_{3-20}$ heterocyclyl group, or a $C_{5-20}$ aryl group. Examples of acylamide groups include, but are not limited to, —NHC(=O)CH$_3$, —NHC(=O)CH$_2$CH$_3$, and —NHC(=O)Ph. R1 and R2 may together form a cyclic structure, as in, for example, succinimidyl, maleimidyl and phthalimidyl.

Acylureido: —N(R1)C(O)NR2C(O)R3 wherein R1 and R2 are independently ureido substituents, for example, hydrogen, a $C_{1-7}$ alkyl group, a $C_{3-20}$ heterocyclyl group, or a $C_{5-20}$ aryl group. R3 is an acyl group as defined for acyl groups. Examples of acylureido groups include, but are not limited to, —NHCONHC(O)H, —NHCONMeC(O)H, —NHCONEtC(O)H, —NHCONMeC(O)Me, —NHCONEtC(O)Et, —NMeCONHC(O)Et, —NMeCONHC(O)Me, —NMeCONHC(O)Et, —NMeCONMeC(O)Me, —NMeCONEtC(O)Et, and —NMeCONHC(O)Ph.

Carbamate: —NR1-C(O)—OR2 wherein R1 is an amino substituent as defined for amino groups and R2 is an ester group as defined for ester groups. Examples of carbamate groups include, but are not limited to, —NH—C(O)—O-Me, —NMe-C(O)—O-Me, —NH—C(O)—O-Et, —NMe-C(O)—O-t-butyl, and —NH—C(O)—O-Ph.

Thioamido (thiocarbamyl): —C(=S)NR1R2, wherein R1 and R2 are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom.

Amino: —NR1R2, wherein R1 and R2 are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, or, in the case of a "cyclic" amino group, R1 and R2, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a C$_{1-7}$ alkyl group, a C$_{3-20}$ heterocyclyl group, or a C$_{5-20}$ aryl group.

Amidine: —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group. An example of an amidine group is —C(=NH)NH$_2$.

Carbazoyl (hydrazinocarbonyl): —C(O)—NN—R1 wherein R1 is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—CH$_2$-Ph.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group (also referred to herein as C$_{1-7}$ alkyl disulfide), a C$_{3-20}$ heterocyclyl group, or a C$_{5-20}$ aryl group. Examples of C$_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group. Examples of sulfinyloxy groups include, but are not limited to, —OS(=O)CH$_3$ and —OS(=O)CH$_2$CH$_3$.

Sulfamino: —NR1S(=O)$_2$OH, wherein R1 is an amino substituent, as defined for amino groups. Examples of sulfamino groups include, but are not limited to, —NHS(=O)$_2$OH and —N(CH$_3$)S(=O)$_2$OH.

Sulfinamino: —NR1S(=O)R, wherein R1 is an amino substituent, as defined for amino groups, and R is a sulfinamino substituent, for example, a C$_{1-7}$ alkyl group, a C$_{3-20}$ heterocyclyl group, or a C$_{5-20}$ aryl group. Examples of sulfinamino groups include, but are not limited to, —NHS(=O)CH$_3$ and —N(CH$_3$)S(=O)C$_6$H$_5$.

Sulfamyl: —S(=O)NR1R2, wherein R1 and R2 are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR1S(=O)$_2$R, wherein R1 is an amino substituent, as defined for amino groups, and R is a sulfonamino substituent, for example, a C$_{1-7}$ alkyl group, a C$_{3-20}$ heterocyclyl group, or a C$_{5-20}$ aryl group. Examples of sulfonamino groups include, but are not limited to, —NHS(=O)$_2$CH$_3$ and —N(CH$_3$)S(=O)$_2$C$_6$H$_5$.

Phosphoramidite: —OP(OR1)-N(R2)$_2$, where R1 and R2 are phosphoramidite substituents, for example, —H, a C$_{1-7}$ alkyl group, a C$_{3-20}$ heterocyclyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR1)-N(R2)$_2$, where R1 and R2 are phosphoramidate substituents, for example, —H, a C$_{1-7}$ alkyl group, a C$_{3-20}$ heterocyclyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a C$_{1-7}$ alkoxy group may be substituted with, for example, a C$_{1-7}$ alkyl (also referred to as a C$_{1-7}$ alkyl-C$_{1-7}$ alkoxy group), for example, cyclohexylmethoxy, a C$_{3-20}$ heterocyclyl group (also referred to as a C$_{5-20}$ heterocyclyl-C$_{1-7}$ alkoxy group), for example phthalimidoethoxy, or a C$_{5-20}$ aryl group (also referred to as a C$_{5-20}$ aryl-C$_{1-7}$ alkoxy group), for example, benzyloxy.

Compounds

The present invention provides compounds according to formula (I):

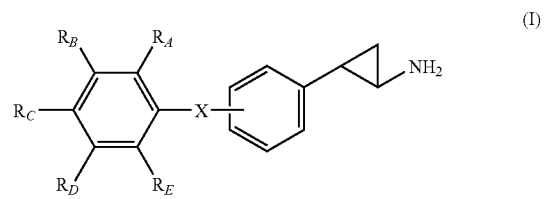

wherein:

X is selected from a bond, O, S, and NH; and $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether;

and isomers, prodrugs and salts thereof.

The present invention also provides compounds according to formula (II):

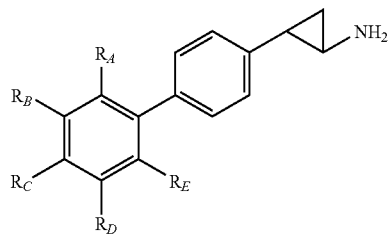

(II)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and isomers, prodrugs and salts thereof.

The present invention further provides compounds according to formula (III):

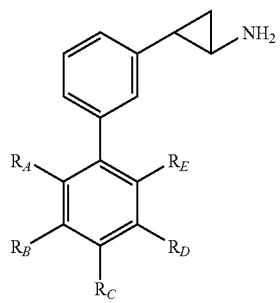

(III)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and isomers, prodrugs and salts thereof.

The present invention additionally provides compounds according to formula (IV):

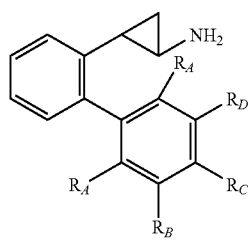

(IV)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and isomers, prodrugs and salts thereof.

The present invention also provides compounds according to formula (V):

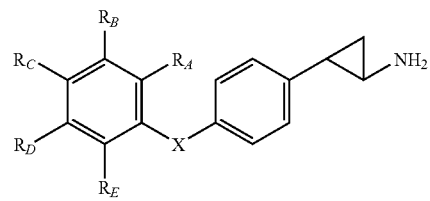

(V)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and X is selected from O, S, and NH; and isomers, prodrugs and salts thereof.

In some embodiments, X is O. In some embodiments, X is S. In some embodiments, $R_C$ is $C_{1-7}$ alkyl such as tert-butyl.

The present invention further provides compounds according to formula (VI):

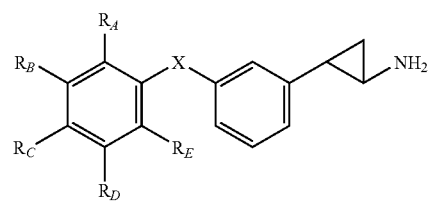

(VI)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and X is selected from O, S, and NH; and isomers, prodrugs and salts thereof.

The present invention additionally provides compounds according to formula (VII):

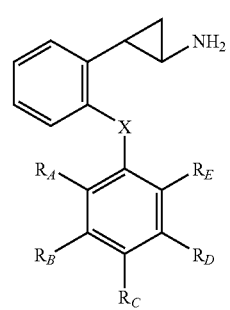

(VII)

wherein $R_A$, $R_B$, $R_C$, $R_D$ and $R_E$ are independently selected from hydrogen, $C_{1-7}$ alkyl, $C_{5-20}$ aryl, $C_{3-20}$ heterocyclyl, $C_{1-7}$ alkoxy, amino, cyano, nitro, halo, haloalkyl, ether and thioether; and X is selected from a O, S, and NH; and isomers, prodrugs and salts thereof.

The present invention also provides compounds according to formula (VIII):

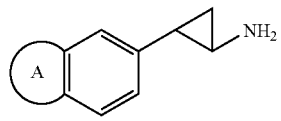

(VIII)

wherein:
A is a $C_5$-$C_6$ aryl, cycloalkenyl or heterocyclyl ring;
and isomers, prodrugs and salts thereof.

The present invention also provides compounds according to formula (IX):

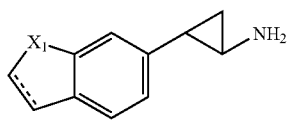

(IX)

wherein $X_1$ is selected from $CH_2$, O, S, and NH; and - - - represents the presence or absence of a bond; and isomers, prodrugs and salts thereof.

The present invention further provides compounds according to formula (X):

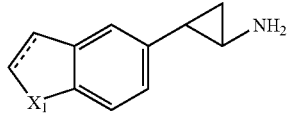

(X)

wherein $X_1$ is selected from $CH_2$, O, S, and NH; and - - - represents the presence or absence of a bond; and isomers, prodrugs and salts thereof.

The present invention further provides compounds according to formula ($X_1$):

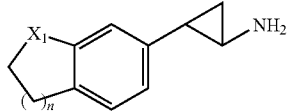

(XI)

wherein $X_1$ is selected from $CH_2$, O, S, and NH; n is 1 or 2; and isomers, prodrugs and salts thereof.

The present invention additionally provides compounds according to formula (XII):

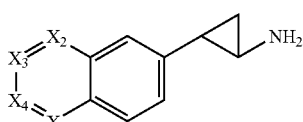

(XII)

wherein $X_2$, $X_3$, $X_4$ and $X_5$ are independently selected from CH and N; and isomers, prodrugs and salts thereof.

The present invention additionally provides compounds according to formula (XIII):

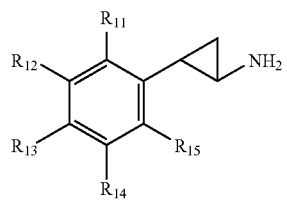

(XIII)

wherein $R_{11}$, $R_{12}$, $R_{13}$, $R_{14}$ and $R_{15}$ are independently selected from hydrogen, $C_{1-7}$ alkyl, $C_{3-20}$ heterocyclyl, $C_{2-7}$ alkoxy, amino, cyano, nitro, ether and thioether; and isomers, prodrugs and salts thereof.

In some embodiments, $R_{13}$ is $C_{2-7}$ alkoxy, such as ethoxy or isopropoxy. In some embodiments, $R_{13}$ is ether, such as phenoxy or benzyloxy. In some embodiments, $R_{13}$ is amino. In some embodiments, $R_{13}$ is thioether.

In some embodiments, $R_{13}$ is $C_{2-7}$ alkoxy (such as ethoxy or isopropoxy). In some embodiments, $R_{13}$ is ether (such as phenoxy or benzyloxy).

The present invention may also provide compounds according to formula (XIV):

(XIV)

where A is a $C_{5-20}$ aryl group and isomers, prodrugs and salts thereof.

In some embodiments, the compound of formula (XIV) is not selected from the following:

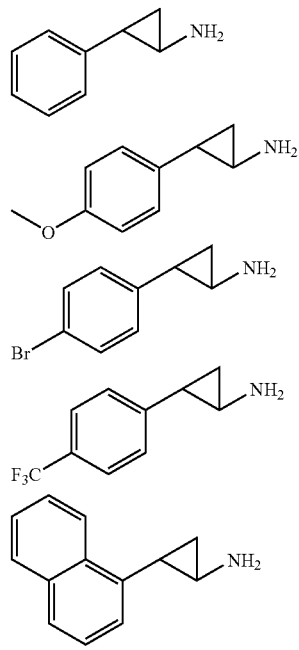

Suitable compounds according to the invention include:
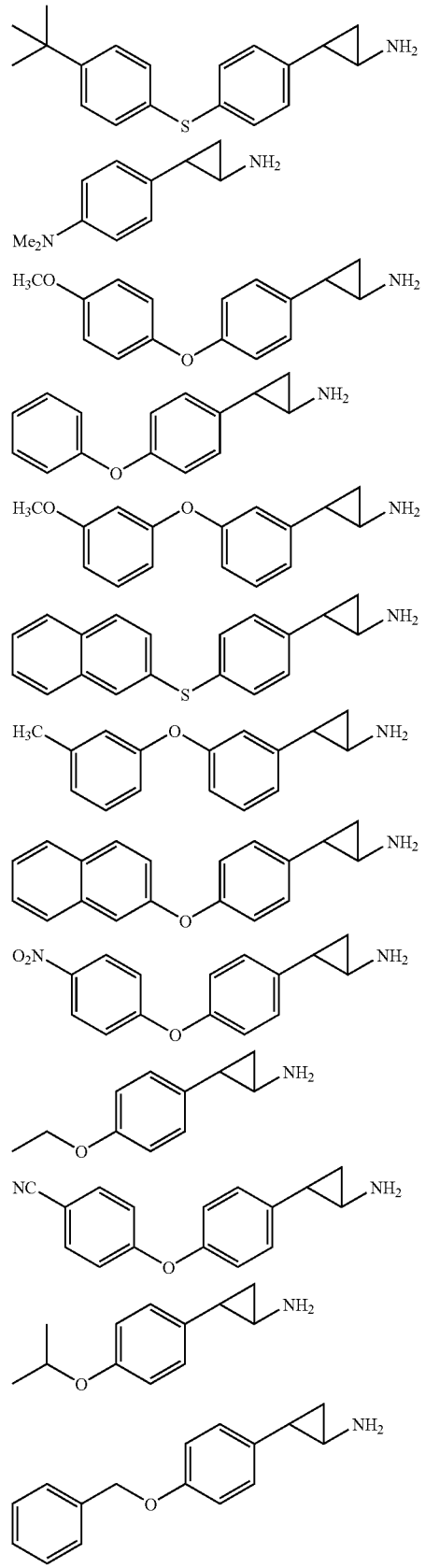
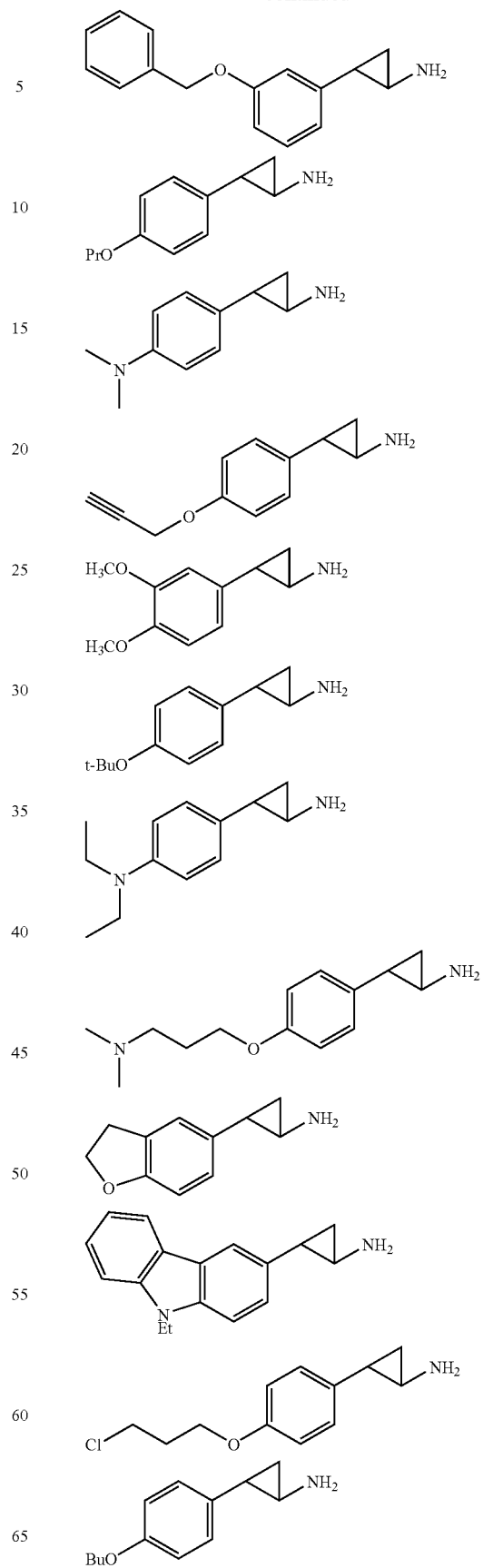

-continued

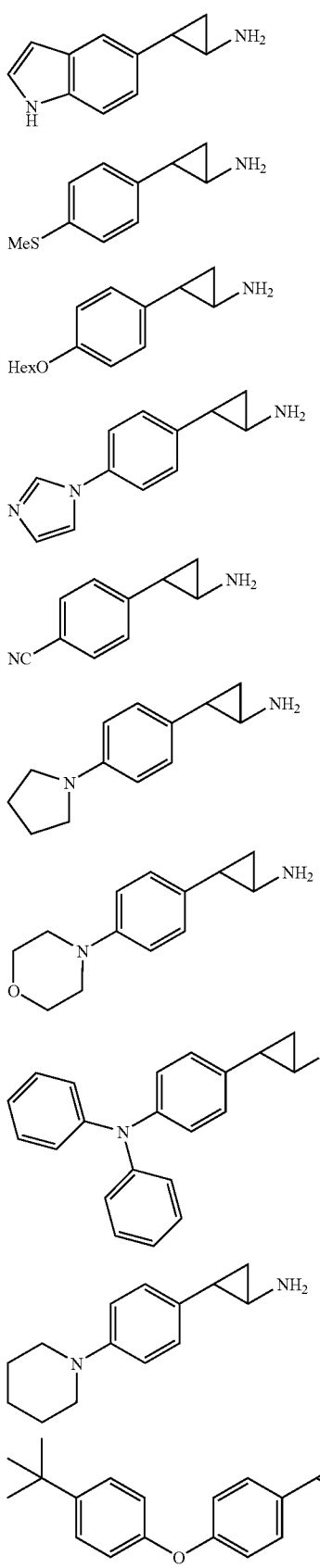

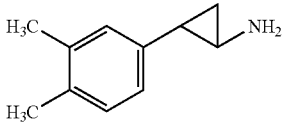

Isomers, Salts, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta chlorophenyl. However, a reference to a class of structures may well include structurally isomeric forms falling within that class (e.g., C$_{1-7}$ alkyl includes n-propyl and iso-propyl; butyl includes n-, iso-, sec-, and tert-butyl; methoxyphenyl includes ortho-, meta-, and paramethoxyphenyl).

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below. It may be convenient or desirable to prepare, purify, and/or handle a corresponding salt of the active compound, for example, a pharmaceutically-acceptable salt. Examples of pharmaceutically acceptable salts are discussed in Berge et al., *J. Pharm. Sci.*, 66, 1-19 (1977). Exemplary pharmaceutically acceptable salts include hydrochloride salts.

For example, if the compound is anionic, or has a functional group which may be anionic (e.g., —COOH may be —COO—), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc). For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, an amine group may be protected, for example, as an amide or a urethane, for example, as: a methyl amide (—NHCO—CH$_3$); a benzyloxy amide (—NHCO—OCH$_2$C$_6$H$_5$, —NHCbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide.

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkylester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$). It may be convenient or desirable to prepare, purify, and/or handle the active compound in the form of a prodrug.

The term "prodrug", as used herein, pertains to a compound which, when metabolized (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexylcarbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis of Compounds

Compounds of the invention may be synthesized according to Scheme 1. For example, an α,β-unsaturated carboxylic acid may be protecting with an acid protecting group (e.g., as an ester such as a methyl ester). Cyclopropanation may be effected by a number of methods, such as use of the Corey-Chaykovsky reagent, or diazomethane in the presence of a catalyst (e.g., palladium(II) acetate). Subsequent deprotection (e.g., via hydrolysis) may be followed by conversion of the carboxylic acid to a primary amine, e.g., via Curtius rearrangement or a Hofmann rearrangement.

Scheme 1.

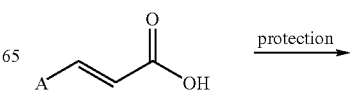

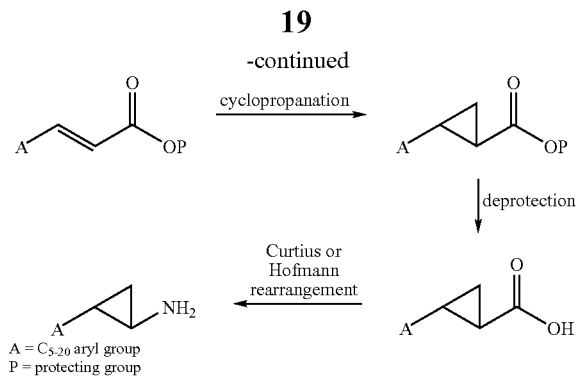

A = $C_{5-20}$ aryl group
P = protecting group

The starting material may be a commercially available α,β-unsaturated acid. Alternatively, an appropriate alkene may be generated from the corresponding aryl aldehyde via an olefination reaction (e.g., the Horner-Wadsworth-Emmons reaction).

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCR Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluating Compounds

A variety of methods can be used to evaluate a compound for ability to inhibit LSD1, MAO-A or MAO-B. Evaluation methods include in vitro assays, in vitro cell-based assays, ex vivo assays and in vivo methods. The methods can evaluate binding activity, or an activity downstream of the enzyme of interest.

For example, in vitro enzymatic assays may be performed in which hydrogen peroxide generated from reoxidation of the FAD cofactor by molecular oxygen by LSD1 or MAOs is monitored, e.g., using a horseradish peroxidase (HRP) coupled assay. The enzyme may be incubated with an appropriate peptide substrate that includes a dimethylated lysine residue, as well as an arylcyclopropylamine compound of the invention. A fluorogenic substrate may be included in the reaction, which upon reaction with $H_2O_2$ produced by the enzyme produces a fluorescent substrate that may be detected. Inhibition kinetics may then be determined by appropriate fitting of the data.

Ex vivo assays may involve treatment of breast, prostate or ovarian cancer cells with an arylcyclopropylamine compound of the invention, followed by detection of changes in transcription levels of certain genes, such as hormone dependent genes (for example, estrogen dependent genes in breast cancer cells) through collection of cellular RNA, conversion to cDNA and quantification by quantitative real time polymerase chain reaction (RT-QPCR). They may further include chromatin immunoprecipitation (ChIP) experiments to investigate the histone methylation statuses and identify the essential proteins present on specific gene promoters after treatment with an arylcyclopropylamine compound in breast, prostate or ovarian cancer cells. Additionally, the cell viability, proliferation, and migration of breast, prostate or ovarian cancer cells may be determined after treatment with an arylcyclopropylamine compound.

Selective Inhibition

"Selective inhibition" means the inhibition of one enzyme to a greater extent than the inhibition of one or more other enzymes. This selectivity is measurable by comparing the ratio of $K_{inact}$ to $K_I$ for the enzymes. Thus, if one wanted to determine if a compound is selective for lysine-specific demethylase 1 (LSD1) compared to monoamine oxidase A (MAO-A), one would determine the ratio of $K_{inact}/K_I$ for LSD1 to the $K_{inact}/K_I$ for MAO-A. If the ratio is greater than 1, then the compound tested exhibits some selectivity for LSD1 in its inhibitory action.

$K_{inact}$ is the maximal rate of inactivation at infinite concentration of inactivator, or the rate of inactivation. $K_I$ is the concentration of inhibitor that yields a rate of inactivation equal to ½ $K_{inact}$.

The compounds of the present invention preferably exhibit a selectivity of greater than 3, 10, 20, 50, 100 or 500 against LSD1 over MAO-A and/or MAO-B.

Uses of the Compounds

The compounds of the present invention are useful as inhibitors of an enzyme comprising an amine oxidase domain, such as LSD1, MAO-A and monoamine oxidase B (MAO-B). In addition, the compounds may be selective inhibitors for LSD1 over MAO-A and/or MAO-B. In one embodiment, the present invention provides a method of inhibiting LSD1 comprising contacting a cell with an effective amount of a compound according to the present invention. In another embodiment, the invention provides a method of inhibiting MAO-A comprising contacting a cell with an effective amount of a compound according to the present invention. In yet another embodiment, the invention provides a method of inhibiting MAO-B comprising contacting a cell with an effective amount of a compound according to the present invention. The cell may be contacted with a pharmaceutical composition comprising a compound according to the present invention. These methods may be practiced in vivo, in vitro, or ex vivo.

The term "effective amount" as used herein, pertains to that amount of an active compound, or a material, composition or dosage form comprising an active compound, which produces some desired effect, such as inhibition of an enzyme.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which a desired therapeutic effect is achieved. For example, treatment may ameliorate the condition or may inhibit the progress of the condition (e.g., reduce the rate of progress or halt the rate of progress).

The term "therapeutically-effective amount" as used herein, pertains to that amount of an active compound, or a material, composition or dosage form comprising an active compound, which is effective for producing some desired therapeutic effect, commensurate with a reasonable benefit/risk ratio.

The term "adjunct" as used herein relates to the use of active compounds in conjunction with known therapeutic means. Such means include cytotoxic regimes of drugs and/or ionizing radiation as used in the treatment of different cancer types.

Cancer

The present invention may provide active compounds which are anticancer agents or adjuncts for treating cancer. One of ordinary skill in the art is readily able to determine whether or not a candidate compound treats a cancerous condition for any particular cell type, either alone or in combination. Examples of cancers include, but are not limited to, lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma and leukemias. Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

The anti cancer treatment defined hereinbefore may be applied as a sole therapy or may involve, in addition to the compound of the invention, conventional surgery or radiotherapy or chemotherapy. The other treatment may be administered simultaneously or sequentially. In some embodiments, the other treatment(s) are administered before or after the compound of the present invention. Chemotherapy may include one or more of the following categories of anti-tumour agents:

(i) other antiproliferative/antineoplastic drugs and combinations thereof, as used in medical oncology, such as:

(a) Alkylating agents, for example: nitrogen mustards such as cyclophosphamide, melphalan, mechlorethamine, ifosfamide and chlorambucil; nitrosoureas such as carmustine (BCNU), lomustine (CCNU) and semustine (methyl-CCNU); ethylenimines/methylmelamines such as triethylenemelamine (TEM), triethylene thiophosphoramide (thiotepa) and hexamethylmelamine (HMM, altretamine); and alkyl sulfonates such as busulfan; and triazines such as dacarbazine (DTIC) and temozolamide.

(b) Antimetabolites, for example: pyrimidine analogs such as 5-fluorouracil, fluorodeoxyuridine, gemcitabine, cytosine arabinoside (AraC, cytarabine), 5-azacytidine and 2,2'-difluorodeoxycytidine; folic acid analogs such as methotrexate, trimetrexate and raltitrexed; purine analogs such as 6-mercaptopurine, 6-thioguanine, azathioprine, 2'-deoxycoformycin (pentostatin), erythrohydroxynonyladenine (EHNA), fludarabine phosphate and 2-chlorodeoxyadenosine (cladribine, 2-CdA); and substituted ureas such as hydroxyurea.

(c) Antitumor antibiotics, for example: anthracyclines such as daunomycin (rubidomycin), doxorubicin (adriamycin), epirubicin, idarubicin, and valrubicin; mitomycin-C, dactinomycin, plicamycin (mithramycin), bleomycin, actimomycin D and mitoxantrone.

(d) Antimitotic agents, for example: vinca alkaloids such vincristine, vinblastine (VLB), vindesine and vinorelbine; taxanes such as docetaxel and paclitaxel; polo-like kinase inhibitors, estramustine and estramustine phosphate.

(e) Platinum based agents, for example: cisplatin, oxaliplatin and carboplatin.

(f) Radiosensitizers such as metronidazole, misonidazole, desmethylmisonidazole, pimonidazole, etanidazole, nimorazole, RSU 1069, EO9, RB 6145, SR4233, nicotinamide, 5-bromodeozyuridine, 5-iododeoxyuridine and bromodeoxycytidine (g) Topoisomerase inhibitors, for example: epipodophyllotoxins such as etoposide and teniposide; amsacrine, camptothecin, topotecan, irinotecan, exatecan, SN-38 and rubitecan.

(h) Enzymes such as L-asparaginase and RNAse A (i) Biological response modifiers such as interferon-alpha, IL-2, G-CSF and GM-CSF (j) Differentiation Agents such as retinoic acid derivatives (e.g., all-trans-retinoic acid (ATRA))

(k) Anthracenediones such as mitoxantrone and AQ4N (l) Methylhydrazine derivatives such as N-methylhydrazine (MIH) and procarbazine (m) Adrenocortical suppressants such as mitotane (o.p'-DDD) and aminoglutethimide (n) Proteasome inhibitors such as bortezomib (ii) cytostatic agents such as antioestrogens (for example tamoxifen, fulvestrant, toremifene, raloxifene, droloxifene and iodoxyfene), Androgens such as testosterone propionate and fluoxymesterone/equivalents, antiandrogens (for example bicalutamide, flutamide, nilutamide, gonadotropin-releasing hormone analogs and cyproterone acetate), LHRH antagonists or LHRH agonists (for example goserelin, leuprorelin and buserelin), progestogens (for example hydroxyprogesterone caproate, medroxyprogesterone acetate and megestrol acetate), aromatase inhibitors (for example as anastrozole, letrozole, vorazole and exemestane) and inhibitors of 5*-reductase such as finasteride; Estrogens such as diethylstilbestrol and ethynyl estradiol/equivalents; Hormones and antagonists such as adrenocorticosteroids/antagonists, prednisone and equivalents, dexamethasone and aminoglutethimide.

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-25 6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signaling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibodies bevacizumab (AvastinT) and ranibizumab (Lucentis) and VEGF receptor tyrosine kinase inhibitors such as 4-(4-bromo-2-fluoroanilino)-6-methoxy-7-(1-methylpiperidin-4-yl-methoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985), pazopanib (Votrient) and SU11248 (sunitinib; WO 01/60814), compounds such as those disclosed in International Patent Applications WO97/22596, WO 97/30035, WO 97/32856 and WO98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukins (such as interleukin 2 or interleukin 4), interferons ($\alpha$, $\beta$, $\beta$), or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

Other Disease States or Conditions

The present invention also may provide methods of treating a central nervous system disorder such as anxiety, depression, and neurodegenerative diseases (e.g. Alzheimer's disease, amyotrophic lateral sclerosis, multiple sclerosis, and Parkinson's disease). The treatment defined hereinbefore may be applied as a sole therapy or may involve administration of active agents in addition to the compound of the invention. The other active agents may be administered simultaneously or sequentially. In some embodiments, the other active agents are administered before or after the compound of the present invention.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichloro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosages

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following general procedures were used in Examples 1-5.

General Procedure for Ullman Coupling:

Under argon, an oven dried round bottom flask was charged with the (thio)phenol (4 mmol, 2 eq) and anhydrous N-Methyl-2-pyrrolidone (5 mL). Cesium carbonate (4 mmol, 2 eq) was added to the stirring solution and it turned cloudy. The alkyl halide (2 mmol, 1 eq) was added, followed by copper (I) bromide (143 mg, 1 mmol, 0.5 eq) and 2,2,6,6-tetramethyl-3,5-heptanedione (41 µL, 0.2 mmol, 0.1 eq). The flask was equipped with a reflux condenser and heated to 70-80° C. for 15-20 hours. After cooling to room temperature, the reaction mixture was diluted with 100 mL of methyl tert-butyl ether and vacuum filtered. The residue was washed with 100 mL of MTBE and the combined filtrates were washed with 100 mL 2N HCl, 100 mL 0.6N HCl, 100 mL 2M NaOH, and 100 mL saturated NaCl. The organic layer was dried over $MgSO_4$, filtered, and concentrated en vacuo. The desired aldehyde was isolated by flash chromatography with silica gel and 10:1 hexanes:ethyl acetate.

General Procedure for Horner-Emmons-Wadsworth Olefination:

Under argon, sodium hydride (92.5 mg, 3.68 mmol, 1.33 eq) was dissolved in 18 mL of anhydrous tetrahydrofuran in an oven dried round bottom flask and cooled to 0° C. with an ice water bath. Methyl diethyl phosphonoacetate (0.65 mL, 3.60 mmol, 1.3 eq) was added dropwise and stirred for 45 minutes while allowing to warm to room temperature. In another round bottom flask under argon, the aldehyde (2.77 mmol, 1.0 eq) was dissolved in 30 mL of anhydrous toluene. This was brought to −78° C. using a dry ice/acetone bath. The flask containing the phosphonate anion was transferred to the second via cannula, dropping the liquid down the side of the flask. THF (3 mL) was used to rinse the flask and quantitatively transfer the phosphonate anion. The reaction was stirred and −78° C. and allowed to warm to room temperature over the course of 6.75 hours. Saturated Rochelle's salt (20 mL) was added and stirred for 10 minutes. Dichloromethane (20 mL) and mili-q water (20 mL) was added and the layers separated. The organic products were extracted with 3×30 mL of $CH_2Cl_2$ and dried over anhydrous $Na_2SO_4$. The solvent was removed under reduced pressure. The desired alkene was isolated by flash chromatography (100% $CH_2Cl_2$).

General Procedure for Cyclopropanation (with $CH_2N_2$):

The diazomethane generator was used. The alkene (1.8 mmol, 1 eq) and palladium (II) acetate catalyst (8.0 mg, 1.6 mol %) were dissolved in 26 mL of diethyl ether in the round bottom flask. 85% Potassium hydroxide pellets (2.8105 g, 42 mmol, 23 eq) was dissolved in 10 mL of water and 15 mL of diethylene glycol monoethyl ether in the distillation chamber. The distillation chamber was brought to 60-70° C. using an oil bath; the cold finger was brought to −72° C. using isopropyl alcohol and dry ice; the round bottom was brought to <−25° C. using dry ice and ethylene glycol. Diazald (3.9032 g, 18 mmol, 10 eq) dissolved in 30 mL of diethyl ether was added dropwise from the addition funnel to the distillation chamber. The produced diazomethane was distilled into the round bottom collecting the gold, clear liquid. After addition, more ether was used to completely transfer the diazomethane. The apparatus was disassembled and the round bottom capped gently and stirred overnight (12-20 hours) allowing to warm to room temperature. The reaction mixture was run over a plug of rinsed celite to remove the catalyst and the solvent removed by rotovap. If the $^1H$ and NMRs indicated that starting alkene was still present, the reaction was repeated using the crude material and same equivalents of reagents in order to produce completely desired cyclopropyl ester.

General Procedure for Saponification with NaOH/MeOH:

To a solution of the methyl ester (1.8 mmol, 1 eq) in methanol (3.2 mL) was added 2M sodium hydroxide with stirring. The reaction was monitored by TLC and upon consumption of the ester, the mixture was poured onto ice (~60 mL) and 12N HCl (1.9 mL) was added dropwise with stirring. The resulting precipitate was isolated by vacuum filtration. The filter cake was washed with portions of ice water until the filtrate was pH neutral. It was dried en vacuo to give the desired acid.

General Procedure for Saponification with LiOH/THF:

To a solution of the methyl ester (1.8 mmol, 1 eq) in tetrahydrofuran (3.2 mL) was added 2M lithium hydroxide with stirring. The reaction was monitored by TLC and upon consumption of the ester, the mixture was poured onto ice (~60 mL) and 12N HCl (1.9 mL) was added dropwise with stirring. The resulting precipitate was isolated by vacuum filtration. The filter cake was washed with portions of ice water until the filtrate was pH neutral. It was dried en vacuo to give the desired acid. If the carboxylic acid was an oil, it was extracted into ethyl acetate (2×30 mL) after acidification and washed with saturated NaCl (10 mL). The organic layer was dried over $MgSO_4$, filtered and concentrated en vacuo.

General Procedure for Curtius Rearrangement:

Diphenylphosphorazidate (1.1 eq) and anhydrous triethylamine (1.4 eq) were added sequentially to a room temperature 0.5M solution of the carboxylic acid in anhydrous tert-butanol. The reaction was heated to 90° C. with an oil bath for 40-48 hours, cooled to room temperature, and concentrated to dryness under reduced pressure. The resulting residue was partitioned between ethyl acetate (15 mL) and 10% aqueous $K_2CO_3$ (10 mL). The organic products were extracted with ethyl acetate (2×15 mL), dried over Na$_2$SO$_4$, filtered, and concentrated en vacuo. The carbamates were purified by flash chromatography (silica gel) with 10:1 hexanes:EtOAc.

Example 1

Synthesis of trans-2-(4-ethoxyphenyl)cyclopropan-1-amine hydrochloride

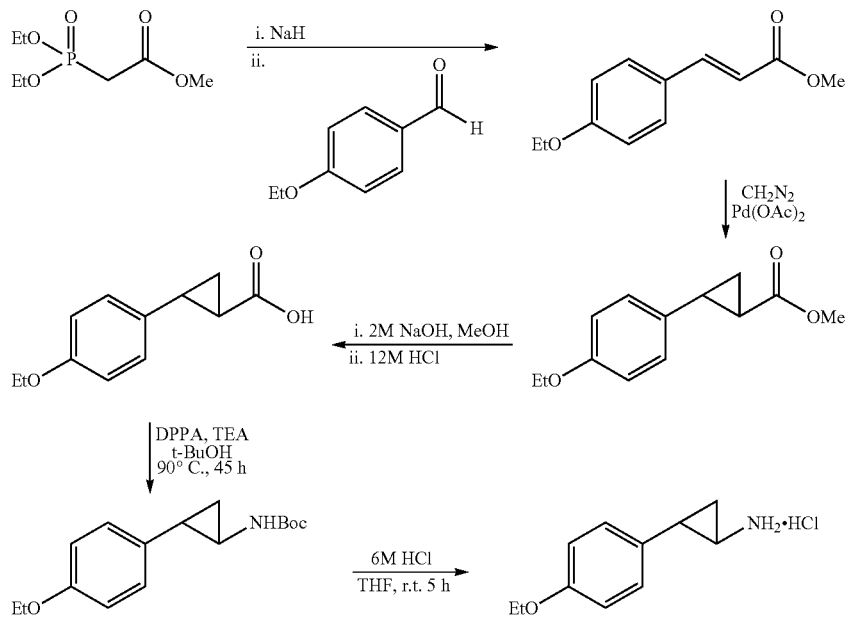

Compound Characterization:

(E)-methyl 3-(4-ethoxyphenyl)acrylate: 0.2714 g, 44%, white solid. $^1$H NMR (300 MHz, CDCl$_3$): δ7.64 (1H, d, J=15.9 Hz), 7.46 (2H, d, J=8.7 Hz), 6.88 (2H, d, J=8.7 Hz), 6.30 (1H, d, J=15.9 Hz), 4.05 (2H, q, J=6.9 Hz), 4.79 (3H, s), 1.42 (3H, t, J=6.9 Hz). $^{13}$C NMR (75 MHz, CDCl$_3$): δ168.0, 161.0, 144.8, 129.9, 127.2, 115.3, 115.1, 63.8, 51.8, 14.9.

Methyl trans-2-(4-ethoxyphenyl)cyclopropanecarboxylate: 0.2862 g, 99%, white solid. $^1$H NMR (400 MHz, CDCl$_3$): δ6.99 (2H, m), 6.79 (2H, m), 3.97 (2H, q, J=7.6 Hz), 3.69 (3H, s), 2.48 (1H, ddd, J=4.2, 4.4, 11.3 Hz), 1.81 (2H, quintet, J=4.2), 1.54 (1H,), 1.38 (3H, t, J=4.2), 1.25 (1H,). $^{13}$C NMR (100 MHz, CDCl$_3$): δ174.2, 157.9, 132.0, 127.5, 114.7, 63.6, 52.0, 26.0, 23.8, 16.9, 15.0.

trans-2-(4-ethoxyphenyl)cyclopropanecarboxylic acid: 0.2100 g, 78%, off-white solid. $^1$H NMR (400 MHz, CDCl$_3$): δ7.02 (2H, m), 6.82 (2H, m), 4.00 (2H, q, J=6.8 Hz), 2.56 (1H, ddd, J=4.0, 6.5, 8.3 Hz), 1.82 (1H, ddd, J=4.0, 5.2, 8.3 Hz), 1.61 (1H, quintet, J=5.2 Hz), 1.40 (3H, t, J=6.8 Hz), 1.35 (ddd, J=4.0, 6.5, 8.3). $^{13}$C NMR (100 MHz, CDCl$_3$): δ180.1, 158.0, 131.5, 127.7, 114.8, 63.7, 26.9, 23.9, 17.4, 15.0.

tert-Butyl trans-[2-(4-ethoxyphenyl)cyclopropyl]carbamate: 0.0398 g, 30%. $^1$H NMR (400 MHz, CDCl$_3$): δ7.06 (2H, m), 6.79 (2H, m), 4.85 (1H, bs), 3.99 (2H, q, J=6.8 Hz) 2.64 (1H, bs), 1.98 (1H, m), 1.45 (9H, s), 1.38 (3H, d, J=6.8 Hz), 1.08 (2H, m). $^{13}$C NMR (100 MHz, CDCl$_3$): δ157.5, 132.8, 127.9, 114.6, 63.6, 28.6, 24.5, 16.0, 15.0.

trans-2-(4-ethoxyphenyl)cyclopropylamine hydrochloride: 0.0307 g, 85%, yellow solid. $^1$H NMR (400 MHz, CDCl$_3$): δ7.70 (1H, d, J=12 Hz), 7.52 (2H, m), 7.38 (2H, m), 6.44 (1H, d, J=12 Hz), 3.81 (3H, s).

Example 2

Synthesis of trans-2-(4-isopropoxyphenyl)cyclopropan-1-amine hydrochloride

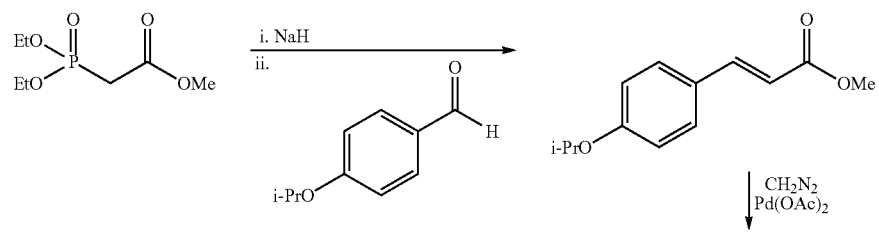

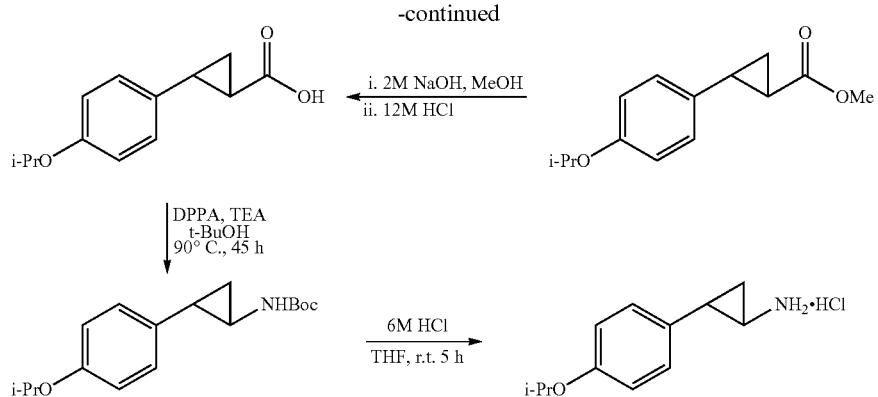

Compound Characterization:

(E)-methyl 3-(4-isopropoxyphenyl)acrylate: 0. g, 98.7%; clear, colorless oil. $^1$H NMR (300 MHz, CDCl$_3$): δ7.62 (1H, d, J=15.9 Hz), 7.37 (2H, m), 6.91 (2H, m), 6.20 (1H, d, J=15.9 Hz), 3.74 (3H, s), 2.96 (6H, s). $^{13}$C NMR (75 MHz, CDCl$_3$): δ168.5, 152.0, 145.6, 130.0, 122.3, 112.2, 112.0, 51.6, 40.3.

Methyl trans-2-(4-isopropoxyphenyl)cyclopropanecarboxylate: 0.4084 g, 100%; clear, yellow oil. $^1$H NMR (300 MHz, CDCl$_3$): δ6.98 (2H, m), 6.78 (2H, m), 4.47 (1H, sep, J=6 Hz), 2.47 (1H, ddd, J=4.3, 4.5, 11.3), 1.82 (1H, q, J=4.2 Hz), 1.54 (1H, q, J=4.2 Hz). $^{13}$C NMR (75 MHz, CDCl$_3$): δ174.1, 156.9, 131.9, 127.6, 116.2, 70.1, 51.9, 26.0, 23.9, 22.2, 16.9.

trans-2-(4-isopropoxyphenyl)cyclopropanecarboxylic acid: 0.3840 g, 78%; white solid. $^1$H NMR (400 MHz, CDCl$_3$): δ7.02 (2H, m), 6.81 (2H, m), 4.50 (1H, sep, J=6.0 Hz), 2.56 (1H, ddd, J=4.0, 6.8, 8.4 Hz), 1.82 (1H, ddd, J=4.0, 5.2, 8.4 Hz), 1.61 (1H, q, J=5.2 Hz), 1.35 (1H, ddd, J=4.0, 6.8, 8.4 Hz), 1.32 (6H, d, J=6.0 Hz). $^{13}$C NMR (100 MHz, CDCl$_3$): δ180.3, 157.0, 131.5, 127.7, 116.2, 70.2, 26.9, 24.0, 22.2, 17.4.

tert-Butyl trans-[2-(4-isopropoxyphenyl)cyclopropyl]carbamate: 0.0765 g, 57%. $^1$H NMR (400 MHz, CDCl$_3$): δ7.05 (2H, m), 6.79 (2H, m), 4.89 (1H, bs), 4.48 (1H, sep, J=6.0 Hz), 2.65 (1H, bs), 1.98 (1H, ddd, J=3.2, 6.4, 9.3 Hz), 1.45 (9H, s), 1.30 (6H, d, J=6.0 Hz), 1.08 (2H, m). $^{13}$C NMR (100 MHz, CDCl$_3$): δ156.4, 132.8, 127.9, 116.1, 70.2, 32.2, 28.6, 24.4, 22.3, 16.0.

trans-2-(4-isopropoxyphenyl)cyclopropylamine hydrochloride: $^1$H NMR (400 MHz, CD$_3$OD): δ7.04 (2H, d, J=8.6 Hz), 6.79 (2H, d, J=8.6 Hz), 4.50 (1H, quintet, J=6.0 Hz), 3.27 (1H, m), 2.71 (1H, quintet, J=4.0 Hz), 2.31 (1H, ddd, J=), 1.34 (1H, ddd, J=), 1.23 (6H, d, J=6.0 Hz). $^{13}$C NMR (100 MHz, CD$_3$OD): δ157.0, 130.4, 127.5, 116.0, 69.8, 30.6, 21.1, 20.7, 12.2.

Example 3

Synthesis of trans-2-(4-phenoxyphenyl)cyclopropylamine hydrochloride

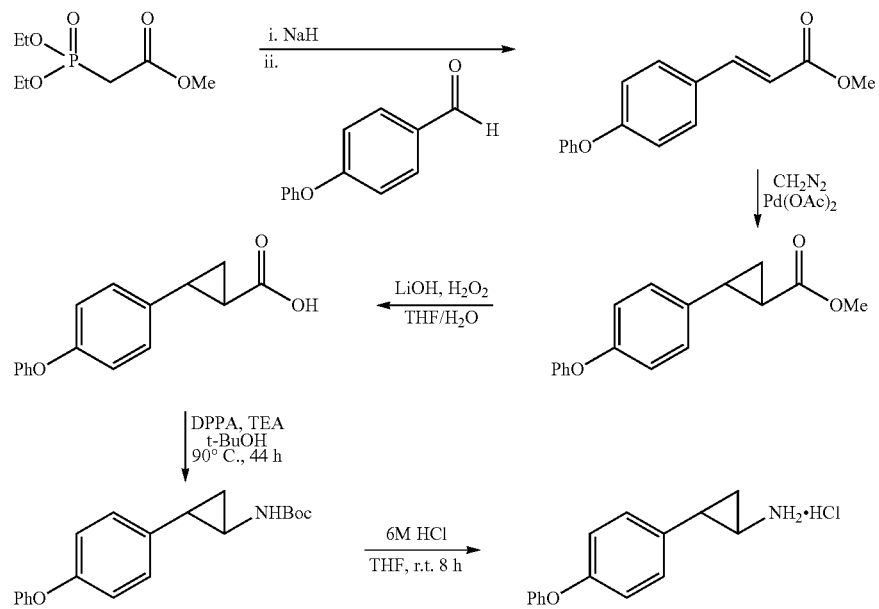

Compound Characterization:

(E)-methyl 3-(4-phenoxyphenyl)acrylate: 0.3945 g, 67%, white solid. $^1$H NMR (300 MHz, CDCl$_3$): δ7.65 (1H, d, J=15.9 Hz), 7.45 (2H, m), 7.32 (2H, m), 7.14 (1H, m), 7.00 (4H, m), 6.33 (1H, d, J=15.9 Hz), 3.77 (3H, s). $^{13}$C NMR (75 MHz, CDCl$_3$): δ167.7, 159.7, 156.3, 144.3, 130.2, 130.0, 129.4, 124.4, 119.9, 118.6, 116.7, 51.9.

Methyl trans-2-(4-phenoxyphenyl)cyclopropanecarboxylate: 0.2788 g, 100%, light gold oil. $^1$H NMR (300 MHz, CDCl$_3$): δ7.28 (2H, m), 7.02 (3H, m), 6.94 (4H, m), 3.69 (3H, s), 2.51 (1H, ddd), 1.86 (1H, ddd), 1.58 (1H, ddd), 1.27 (1H, ddd). $^{13}$C NMR (75 MHz, CDCl$_3$): δ174.1, 157.6, 156.1, 135.1, 130.0, 127.9, 123.4, 119.3, 118.9, 52.1, 30.0, 26.0, 24.1, 17.1.

trans-2-(4-phenoxyphenyl)cyclopropanecarboxylic acid: 0.1481 g, 58%, white solid. $^1$H NMR (300 MHz, CD$_3$OD): δ7.27 (2H, m), 7.04 (3H, m), 6.89 (4H, m), 5.05 (1H, bs), 2.44 (1H, ddd), 1.78 (1H, ddd), 1.50 (1H, ddd), 1.28 (1H, ddd). $^{13}$C NMR (75 MHz, CD$_3$OD): δ175.9, 157.6, 156.1, 135.3, 129.7, 127.5, 123.1, 118.9, 118.5, 25.5, 23.8, 16.2.

tert-Butyl trans-[2-(4-phenoxyphenyl)cyclopropyl]carbamate: 0.0351 g, 29%, yellow oil. $^1$H NMR (300 MHz, CDCl$_3$): δ7.33 (2H, m), 7.10 (3H, m), 6.93 (4H, m), 4.85 (1H, bs), 2.69 (1H, m), 2.03 (1H, m), 1.46 (9H, s), 1.15 (2H, m). $^{13}$C NMR (75 MHz, CDCl$_3$): δ157.9, 156.6, 155.5, 136.0, 129.9, 128.1, 123.2, 119.4, 118.7, 79.9, 32.6, 28.6, 24.8, 16.3.

trans-2-(4-phenoxyphenyl)cyclopropylamine hydrochloride: 0.0250 g, 88%, yellow solid. $^1$H NMR (300 MHz, CD$_3$OD): δ7.33 (2H, m), 7.30 (3H, m), 6.93 (4H, m), 4.87 (3H, s), 2.82 (1H, ddd), 2.39 (1H, ddd), 1.42 (1H, ddd), 1.29 (1H, ddd). $^{13}$C NMR (75 MHz, CD$_3$OD): δ157.5, 156.5, 133.5, 129.7, 127.8, 123.3, 118.8, 118.6, 30.7, 20.8, 12.5.

Example 4

Synthesis of trans-2-(4-(benzyloxy)phenyl)cyclopropylamine hydrochloride

Compound Characterization:

(E)-methyl 3-(4-(benzyloxy)phenyl)acrylate: 1.1199 g, 83%, white solid. $^1$H NMR (300 MHz, CDCl$_3$): δ7.64 (1H, d, J=16 Hz), 7.41 (7H, m), 6.96 (2H, d, J=8.7 Hz), 6.30 (1H, d, J=16 Hz), 5.08 (2H, s), 3.78 (3H, s). $^{13}$C NMR (75 MHz, CDCl$_3$): δ144.4, 129.7, 128.6, 128.1, 127.4, 115.3, 115.1, 70.0, 51.5.

Methyl trans-2-(4-(benzyloxy)phenyl)cyclopropanecarboxylate: 0.2982 g, 100%, off-white solid. $^1$H NMR (300 MHz, CDCl$_3$): δ 7.37 (4H, m), 7.05 (2H, m), 6.92 (2H, m), 5.04 (2H, s), 3.73 (3H, s), 2.53 (1H, ddd), 1.86 (1H, ddd), 1.59 (1H, ddd), 1.29 (1H, ddd). $^{13}$C NMR (75 MHz, CDCl$_3$): δ147.2, 157.8, 137.3, 132.5, 128.9, 128.2, 127.7, 115.2, 70.3, 52.1, 26.0, 24.0, 17.0.

trans-2-(4-(benzyloxy)phenyl)cyclopropanecarboxylic acid: 0.2166 g, 76%, white solid. $^1$H NMR (300 MHz, CDCl$_3$): δ7.30 (5H, m), 7.02 (2H, m), 6.90 (2H, m), 5.03 (2H, s), 2.40 (1H, ddd), 1.74 (1H, ddd), 1.47 (1H, ddd), 1.28 (1H, ddd).

tert-Butyl trans-[2-(4-(benzyloxy)phenyl)cyclopropyl]carbamate: 0.0390 g, 27%, yellow solid. $^1$H NMR (300 MHz, CDCl$_3$): δ7.39 (5H, m), 7.07 (2H, d, J=8.7 Hz), 6.87 (2H, d, J=8.7 Hz), 5.03 (2H, s), 4.82 (1H, bs), 2.65 (1H, m), 1.99 (1H, ddd), 1.45 (9H, s), 1.09 (2H, m). $^{13}$C NMR (75 MHz, CDCl$_3$): δ157.5, 137.4, 133.3, 128.8, 128.1, 128.0, 127.7, 115.0, 70.3, 32.4, 29.9, 28.7, 24.6, 16.1.

trans-2-(4-(benzyloxy)phenyl)cyclopropylamine hydrochloride: 0.0281 g, 87%, yellow solid. $^1$H NMR (300 MHz, CD$_3$OD): δ7.36 (5H, m), 7.09 (2H, d, J=8.7 Hz), 6.93 (2H, d, J=8.7 Hz), 5.05 (2H, s), 4.87 (3H, s), 2.75 (1H, ddd), 2.319 (1H, ddd), 1.31 (2H, m). $^{13}$C NMR (75 MHz, CD$_3$OD): δ158.0, 137.5, 130.7, 128.3, 127.7, 127.5, 127.3, 115.0, 69.8, 30.6, 20.7, 12.2.

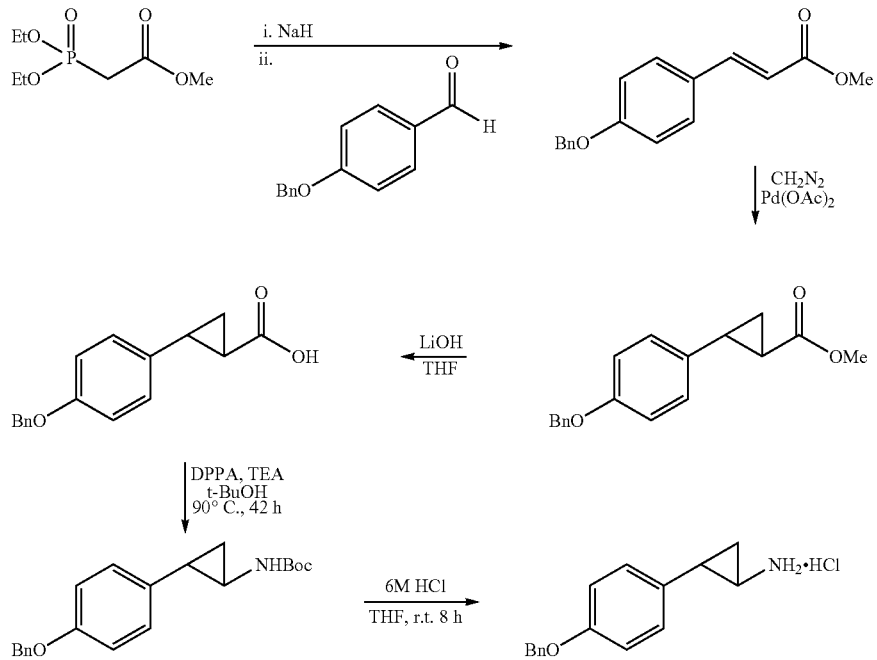

Example 5

Synthesis of trans-2-(4-(4-tert-butylphenylthio)phenyl)cyclopropylamine hydrochloride

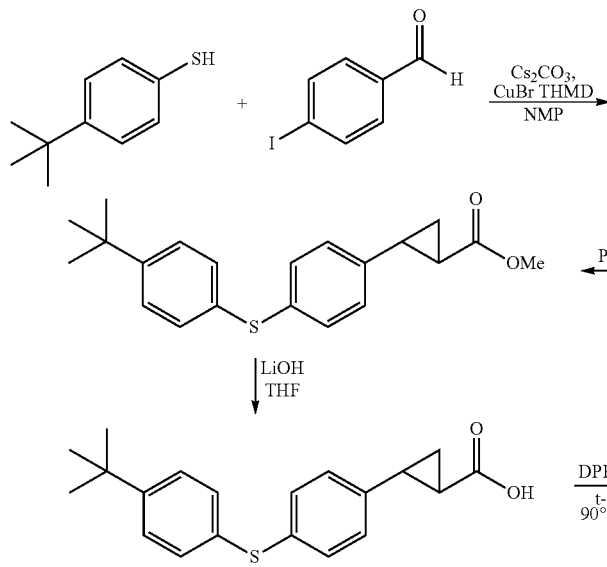
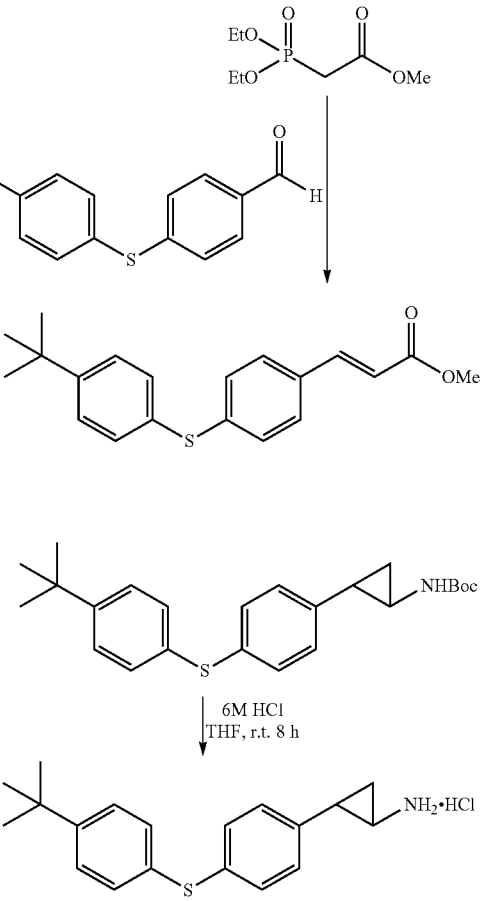

Compound Characterization:

4-(4-tert-butylphenylthio)benzaldehyde: 0.0650 g, 54%, gold oil. $^1$H NMR (400 MHz, CDCl$_3$): δ9.88 (1H, s), 7.69 (2H, d, J=8.4 Hz), 7.44 (4H, m), 7.20 (2H, d, J=8.4 Hz), 1.34 (9H, s). $^{13}$C NMR (100 MHz, CDCl$_3$): δ191.2, 152.7, 148.0, 134.4, 133.5, 130.1, 127.3, 126.9, 126.7, 34.8, 31.2.

(E)-methyl 3-(4-(4-tert-butylphenylthio)phenyl)acrylate: 0.2975 g, 76%, white solid. $^1$H NMR (300 MHz, CDCl$_3$): δ7.63 (1H, d, J=15.9), 7.38 (6H, m), 7.19 (2H, m), 6.37 (1H, d, J=15.9 Hz), 3.79 (3H, s), 1.33 (9H, s). $^{13}$C NMR (75 MHz, CDCl$_3$): δ167.3, 151.6, 144.0, 141.1, 133.1, 131.8, 129.2, 128.4, 128.4, 126.5, 117.0, 51.6, 34.6, 31.1.

Methyl trans-2-(4-(4-tert-butylphenylthio)phenyl)cyclopropanecarboxylate: 0.2462 g, 94%, gold oil. $^1$H NMR (300 MHz, CDCl$_3$): δ7.25 (5H, m), 6.99 (2H, m), 3.69 (3H, s), 2.41 (1H, ddd), 1.87 (1H, ddd), 1.59 (1H, ddd), 1.29 (10H, m). $^{13}$C NMR (100 MHz, CDCl$_3$): δ173.9, 150.6, 139.1, 134.5, 132.4, 131.2, 127.2, 126.5, 52.2, 34.8, 31.5, 26.2, 24.3, 17.3.

trans-2-(4-(4-tert-butylphenylthio)phenyl)cyclopropanecarboxylic acid: 0.1661 g, 73%, yellow oil. $^1$H NMR (300 MHz, CD$_3$OD): δ7.14 (8H, m), 4.99 (1H, bs), 2.41 (1H, ddd), 1.79 (1H, ddd), 1.49 (1H, ddd), 1.24 (10H, m). $^{13}$C NMR (75 MHz, CD$_3$OD): δ175.6, 150.5, 139.4, 134.5, 132.3, 131.1, 130.7, 126.9, 126.2, 34.2, 30.6, 25.6, 24.0, 16.4.

tert-Butyl trans-[2-(4-(4-tert-butylphenylthio)phenyl]carbamate: 0.0344 g, 29%, yellow oil. $^1$H NMR (300 MHz, CDCl$_3$): δ7.29 (6H, m), 7.06 (2H, d, J=8.4 Hz), 4.85 (1H, bs), 2.70 (1H, m), 2.01 (1H, m), 1.24 (18H, m), 0.95 (2H, m). $^{13}$C NMR (75 MHz, CDCl$_3$): δ150.3, 140.1, 133.4, 131.5, 130.7, 130.3, 127.5, 127.1, 126.4, 34.7, 32.9, 31.5, 29.9, 28.6, 25.1, 16.6.

trans-2-(4-(4-tert-butylphenylthio)phenyl)cyclopropylamine hydrochloride: 0.019 g, 66%, yellow solid. $^1$H NMR (300 MHz, CD$_3$OD): δ7.21 (8H, m), 4.86 (3H, s), 2.83 (1H, ddd), 2.35 (1H, ddd), 1.31 (11H, m).

Example 6

Kinetic parameters for inactivation of LSD1, MAO B and MAO A by arylcyclopropylamine compounds Substrate Synthesis A peptide containing the first 21 amino acids of the N-terminal tail of histone H3 incorporating dimethylated lysine at residue 4 (H-ART(dimethyl-Lys)QTARKSTG-GKAPRKQLAGYG-NH$_2$) was prepared using standard Fmoc/t-Bu solid phase peptide synthesis. The C-terminal GYG was added to allow for quantification of the peptide concentration. Reverse-phase C$_{18}$ semipreparative HPLC was used to purify the peptide and the identity confirmed by MALDI-MS (observed 2559.7, expected 2557.5).

Enzymatic Assays

The peroxide production generated from reoxidation of the FAD cofactor by molecular oxygen by LSD1 or MAOs was monitored using a horseradish peroxidase (HRP) coupled assay (FIG. 1). Amplex red was used as the fluorogenic electron acceptor and the fluorescence (excitation 560 nm, emission 590 nm) was measured using a Molecular Devices Spectra Max Gemini EM plate reader. The inhibition kinetics were determined by fitting the progress curves to eq. 1 describing time-dependent inactivation to determine $k_{obs}$:

$$\text{product} = (v_i/k_{obs})(1-e^{-k_{obs}t}) \qquad (1)$$

where $v_i$ is the initial rate prior to inactivation, t is time and $k_{obs}$ is the observed rate of inactivation. The resulting values were plotted as a function of inhibitor concentration to obtain values of $K_i$ and $k_{inact}$ according to eq. 2.

$$k_{obs} = \frac{k_{inact}[I]}{K_I + [I]} \qquad (2)$$

where $k_{inact}$ is the maximal rate of inactivation and $K_i$ is the inhibitor concentration that yields half that rate of inactivation. Results are given in Table 1.

The invention claimed is:

1. A pharmaceutical composition comprising a compound according to formula (XIII) or a pharmaceutically acceptable salt thereof:

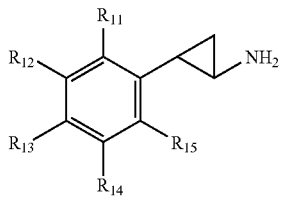

(XIII)

wherein $R_{11}$, $R_{12}$, $R_{13}$, $R_{14}$ and $R_{15}$ are independently selected from hydrogen, $C_{1-7}$ alkyl, $C_{3-20}$ heterocyclyl, $C_{2-7}$ alkoxy, amino, cyano, nitro, $C_{3-20}$ heterocyclyloxy, $C_{5-20}$ aryloxy, $C_{5-20}$ arylalkyloxy and thioether; and a pharmaceutically acceptable carrier.

2. The composition of claim 1, wherein $R_{13}$ is $C_{2-7}$ alkoxy.

3. The composition of claim 2, wherein $R_{13}$ is ethoxy.

4. The composition of claim 2, wherein $R_{13}$ is isopropoxy.

5. The composition of claim 1, wherein $R_{13}$ is $C_{5-20}$ aryloxy or $C_{5-20}$ arylalkyloxy.

6. The composition of claim 5, wherein $R_{13}$ is phenoxy.

7. The composition of claim 5, wherein $R_{13}$ is benzyloxy.

8. A pharmaceutical composition comprising a compound selected from:

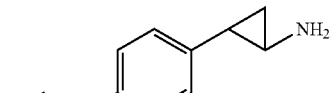

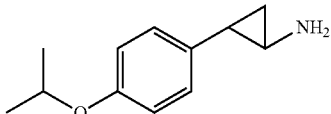

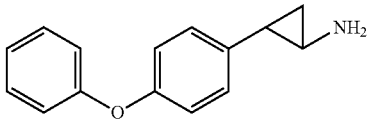

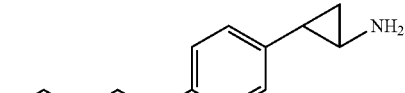 and

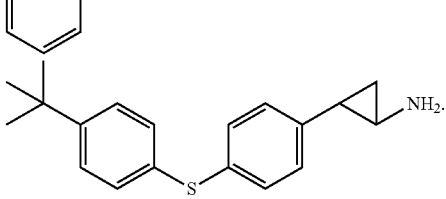

and a pharmaceutically acceptable carrier.

* * * * *